(12) United States Patent  
Cao et al.

(10) Patent No.: US 10,085,798 B2
(45) Date of Patent: Oct. 2, 2018

(54) ABLATION ELECTRODE WITH TACTILE SENSOR

(75) Inventors: Hong Cao, Savage, MN (US); Chou Thao, Brooklyn Park, MN (US); Saurav Paul, Minnetonka, MN (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 1288 days.

(21) Appl. No.: 11/647,279

(22) Filed: Dec. 29, 2006

(65) Prior Publication Data

US 2008/0161796 A1 Jul. 3, 2008

(51) Int. Cl.
*A61B 18/14* (2006.01)
*A61B 90/00* (2016.01)

(52) U.S. Cl.
CPC .... *A61B 18/1492* (2013.01); *A61B 2090/065* (2016.02)

(58) Field of Classification Search
CPC ...................... A61B 18/1492; A61B 2090/065
USPC ........................... 606/41, 45–50; 607/96–101
See application file for complete search history.

(56) References Cited

U.S. PATENT DOCUMENTS

| | | |
|---|---|---|
| 4,074,718 A | 2/1978 | Morrison |
| 4,495,236 A | 1/1985 | Obara |
| 4,600,017 A | 7/1986 | Schroeppel |
| 4,682,596 A | 7/1987 | Bales et al. |
| 4,799,495 A | 1/1989 | Hawkins |
| 4,911,174 A | 3/1990 | Pederson et al. |
| 4,976,711 A | 12/1990 | Parins |

(Continued)

FOREIGN PATENT DOCUMENTS

| | | |
|---|---|---|
| EP | 1491139 | 12/2004 |
| JP | 06-154154 | 6/1994 |

(Continued)

OTHER PUBLICATIONS

Peratech Ltd. (website page), QTC Pills, Retrofittable Components for Improved Switching Performance, Jan. 2004, www.peratech.co.uk.

(Continued)

*Primary Examiner* — Michael Peffley
*Assistant Examiner* — Samantha Good
(74) *Attorney, Agent, or Firm* — Wiley Rein LLP

(57) ABSTRACT

A catheter assembly for assessing contact between the catheter assembly and tissue is disclosed. The assembly includes a catheter shaft and a pressure sensitive conductive composite member whose electrical resistance varies with pressure applied to the catheter assembly. The assembly also includes at least one measurement terminal to permit the measurement of changes in the electrical characteristics of the pressure sensitive conductive composite member. The assembly may optionally include a measurement device to measure resistance, impedance and/or other electrical characteristics. The assembly may utilize a reference electrode secured to the patient's tissue, which permits the measurement device to measure changes between the reference electrode and the at least one measurement terminal. Optionally, the assembly may include a conductive outer layer. Also disclosed are sensor assemblies, contact sensor, methods of contact sensing, and methods of manufacturing relating to the use of pressure sensitive conductive composites.

7 Claims, 14 Drawing Sheets

(56) References Cited

U.S. PATENT DOCUMENTS

| | | | |
|---|---|---|---|
| 4,991,588 A | 2/1991 | Pflueger | |
| 5,028,394 A | 7/1991 | Lowell, Jr. et al. | |
| 5,327,905 A | 7/1994 | Avitall | |
| 5,341,807 A | 8/1994 | Nardella | |
| 5,354,279 A | 10/1994 | Hofling | |
| 5,372,603 A | 12/1994 | Acker et al. | |
| 5,382,247 A | 1/1995 | Cimino et al. | |
| 5,396,887 A | 3/1995 | Imran | |
| 5,405,346 A | 4/1995 | Grundy et al. | |
| 5,409,008 A | 4/1995 | Svenson et al. | |
| 5,447,539 A | 9/1995 | Marchlinski | |
| 5,472,441 A | 12/1995 | Edwards et al. | |
| 5,536,245 A | 7/1996 | Dahlbeck | |
| 5,545,161 A | 8/1996 | Imran | |
| 5,643,197 A | 7/1997 | Brucker | |
| 5,685,878 A | 11/1997 | Falwell et al. | |
| 5,697,925 A | 12/1997 | Taylor | |
| 5,782,828 A | 7/1998 | Chen et al. | |
| 5,836,990 A | 11/1998 | Li | |
| 5,868,737 A | 2/1999 | Taylor et al. | |
| 5,893,848 A | 4/1999 | Negus | |
| 5,895,355 A | 4/1999 | Schaer | |
| 5,913,854 A | 6/1999 | Maguire et al. | |
| 5,947,905 A | 9/1999 | Hadjicostis et al. | |
| 5,997,532 A | 12/1999 | McLaughlin et al. | |
| 6,013,074 A | 1/2000 | Taylor | |
| 6,032,077 A | 2/2000 | Pomeranz | |
| 6,039,731 A | 3/2000 | Taylor et al. | |
| 6,063,022 A | 5/2000 | Ben-Haim | |
| 6,066,139 A | 5/2000 | Ryan et al. | |
| 6,078,830 A | 6/2000 | Levin | |
| 6,110,100 A * | 8/2000 | Talpade | 600/37 |
| 6,113,592 A | 9/2000 | Taylor | |
| 6,113,593 A | 9/2000 | Tu et al. | |
| 6,127,672 A | 10/2000 | Danisch | |
| 6,171,304 B1 | 1/2001 | Netherly et al. | |
| 6,210,406 B1 | 4/2001 | Webster | |
| 6,217,573 B1 | 4/2001 | Webster | |
| 6,217,574 B1 | 4/2001 | Webster | |
| 6,221,023 B1 | 4/2001 | Matsuba et al. | |
| 6,241,724 B1 | 6/2001 | Fleischman et al. | |
| 6,246,898 B1 | 6/2001 | Vesely et al. | |
| 6,264,653 B1 | 7/2001 | Falwell | |
| 6,272,371 B1 | 8/2001 | Shlomo | |
| 6,291,568 B1 | 9/2001 | Lussey et al. | |
| 6,304,776 B1 | 10/2001 | Muntermann | |
| 6,322,558 B1 | 11/2001 | Taylor et al. | |
| 6,325,799 B1 | 12/2001 | Goble | |
| 6,391,024 B1 | 5/2002 | Sun et al. | |
| 6,423,057 B1 | 7/2002 | He et al. | |
| 6,470,236 B2 | 10/2002 | Ohtsuki | |
| 6,495,069 B1 | 12/2002 | Lussey et al. | |
| 6,616,657 B2 | 9/2003 | Simpson et al. | |
| 6,620,159 B2 | 9/2003 | Hedge | |
| 6,638,222 B2 | 10/2003 | Chandrasekaran et al. | |
| 6,646,540 B1 | 11/2003 | Lussey | |
| 6,689,128 B2 | 2/2004 | Sliwa et al. | |
| 6,696,844 B2 | 2/2004 | Wong et al. | |
| 6,701,931 B2 | 3/2004 | Sliwa et al. | |
| 6,730,082 B2 | 5/2004 | Messing et al. | |
| 6,800,986 B2 | 10/2004 | Yamauchi | |
| 6,837,886 B2 | 1/2005 | Collins | |
| 6,845,264 B1 | 1/2005 | Skladnev et al. | |
| 6,882,885 B2 | 4/2005 | Levy, Jr. et al. | |
| 6,936,047 B2 | 8/2005 | Nasab et al. | |
| 6,974,457 B2 | 12/2005 | Gibson | |
| 6,999,821 B2 | 2/2006 | Jenney et al. | |
| 7,011,410 B2 | 3/2006 | Bolger | |
| 7,060,965 B2 | 6/2006 | Vidovic et al. | |
| 7,883,508 B2 * | 2/2011 | Thao et al. | 606/40 |
| 8,021,361 B2 | 9/2011 | Paul | |
| 8,226,648 B2 | 7/2012 | Paul | |
| 2001/0034501 A1 | 10/2001 | Tom | |
| 2002/0077627 A1 * | 6/2002 | Johnson et al. | 606/41 |
| 2002/0115958 A1 | 8/2002 | Nyhart | |
| 2002/0123749 A1 * | 9/2002 | Jain | 606/41 |
| 2002/0147446 A1 | 10/2002 | Ein-Gal | |
| 2003/0056351 A1 | 3/2003 | Wilkie | |
| 2003/0130615 A1 | 7/2003 | Tom | |
| 2003/0204184 A1 | 10/2003 | Ferek-Patric | |
| 2004/0039298 A1 | 2/2004 | Abreu | |
| 2004/0059328 A1 * | 3/2004 | Daniel et al. | 606/41 |
| 2004/0111087 A1 * | 6/2004 | Stern et al. | 606/41 |
| 2004/0133092 A1 | 7/2004 | Kain | |
| 2004/0133166 A1 | 7/2004 | Moberg et al. | |
| 2004/0150322 A1 | 8/2004 | Busta | |
| 2004/0199156 A1 | 10/2004 | Rioux et al. | |
| 2004/0210214 A1 * | 10/2004 | Knowlton | A61B 18/14 606/41 |
| 2004/0215185 A1 | 10/2004 | Truckai | |
| 2004/0217674 A1 | 11/2004 | Bianchini | |
| 2004/0220511 A1 | 11/2004 | Scott et al. | |
| 2005/0049583 A1 | 3/2005 | Swanson et al. | |
| 2005/0090881 A1 | 4/2005 | Frank et al. | |
| 2005/0119650 A1 | 6/2005 | Sanders et al. | |
| 2005/0131390 A1 * | 6/2005 | Heinrich et al. | 606/1 |
| 2005/0137662 A1 * | 6/2005 | Morris et al. | 607/101 |
| 2005/0159739 A1 | 7/2005 | Paul et al. | |
| 2005/0192568 A1 | 9/2005 | Truckai et al. | |
| 2005/0267332 A1 | 12/2005 | Paul | |
| 2005/0267458 A1 | 12/2005 | Paul | |
| 2005/0267467 A1 | 12/2005 | Paul et al. | |
| 2006/0084968 A1 | 4/2006 | Truckai et al. | |
| 2006/0084969 A1 | 4/2006 | Truckai et al. | |
| 2006/0095022 A1 | 5/2006 | Moll et al. | |
| 2006/0111706 A1 | 5/2006 | Truckai et al. | |
| 2006/0137464 A1 * | 6/2006 | Baudendistel | 73/779 |
| 2006/0147700 A1 | 7/2006 | Papakostas | |
| 2006/0249705 A1 | 11/2006 | Wang et al. | |
| 2006/0264831 A1 | 11/2006 | Skwarek et al. | |
| 2006/0278248 A1 | 12/2006 | Viswanathan | |
| 2006/0287602 A1 | 12/2006 | O'Brien et al. | |
| 2006/0287700 A1 * | 12/2006 | White | A61B 5/0031 607/127 |
| 2007/0078484 A1 | 4/2007 | Talarico | |
| 2007/0197896 A1 | 8/2007 | Moll et al. | |
| 2007/0244520 A1 | 10/2007 | Ferren et al. | |
| 2007/0250050 A1 | 10/2007 | LaFontaine et al. | |
| 2007/0265610 A1 | 11/2007 | Thapliyal et al. | |
| 2007/0287999 A1 | 12/2007 | Malecki et al. | |
| 2007/0299492 A1 | 12/2007 | Zhang et al. | |
| 2008/0161794 A1 | 7/2008 | Wang | |
| 2008/0161796 A1 | 7/2008 | Cao | |
| 2008/0161889 A1 * | 7/2008 | Paul et al. | 607/102 |
| 2008/0255629 A1 | 10/2008 | Jenson | |
| 2008/0275442 A1 * | 11/2008 | Paul et al. | 606/41 |
| 2009/0158852 A1 * | 6/2009 | Paul et al. | 73/723 |
| 2010/0168620 A1 | 7/2010 | Klimovitch et al. | |

FOREIGN PATENT DOCUMENTS

| | | |
|---|---|---|
| JP | 09-135905 | 5/1997 |
| WO | 1995/10978 | 4/1995 |
| WO | 1997/018754 | 5/1997 |
| WO | 1998/17185 | 4/1998 |
| WO | 2004/098694 | 11/2004 |
| WO | 2005039835 | 5/2005 |

OTHER PUBLICATIONS

PCT International Search Report and Written Opinion of the International Searching Authority for PCT/US07/88729 dated May 16, 2008.

Biopac Systems, Inc., "Micro Pressure Measurement System—Product Overview," 39 pages, 2000.

"Fiber Optic Interferometer Fabry-Perot," available from http://physics.nad.ru/Physics/English/ifp_txt.htm at least as early as Oct. 15, 2007, 4 pages.

Medical Product Manufacturing News "Need to Know," 1 page, Sep. 2007.

Bioseb: Samba—Blood Pressure System, available from http://www.bioseb.com/anglais/default/item_id=904_cat_id=3+Samba%20-%

(56) References Cited

OTHER PUBLICATIONS

20Blood%20Pressure%System.php at least as early as Oct. 15, 2007, 3 pages.
Samba Sensors, "The Samba Technology," available from http://www.samba.se/index2.cfm?PageID=45 at least as early as Oct. 15, 2007, 1 page.
Samba Sensors, "Publications related to Samba Sensors AB," 3 pages.
PCT International Search Report and Written Opinion of the International Searching Authority for PCT/US06/39881 dated Jun. 30, 2008, 4 pages.
PCT International Search Report and Written Opinion of the International Searching Authority for PCT/US07/80981 dated Apr. 16, 2008, 6 pages.
PCT International Search Report and Written Opinion of the International Searching Authority for PCT/US07/80983 dated Apr. 2, 2008, 5 pages.
PCT International Search Report and Written Opinion of the International Searching Authority for PCT/US06/42119 dated Sep. 13, 2007, 5 pages.
PCT International Search Report and Written Opinion of the International Searching Authority for PCT/US07/88723 dated Jul. 7, 2008.
PCT International Search Report and Written Opinion of the International Searching Authority for PCT/US07/88680 dated Jul. 2, 2008.
Ghosh et al. Development of Layered Functional Fiber Based Micro-Tubes. National Textile Center Annual Report: Nov. 2005. Retrieved from the Internet on Jun. 24, 2008: <http://www.ntcresearch.org/pdf-rpts/AnRp05/F02-NS05-A5.pdf>.
NuSil R-2637 Product Profile Dec. 12, 2006 (Dec. 12, 2006).
PCT International Search Report of the International Searching Authority for PCT/US07/89099 dated Jul. 7. 2008.
Olaf J. Eick, et al., "The LETR-Principle: A Novel Method to Assess Electrode-Tissue Contact in Radiofrequency Ablation," Jul. 1998.
Measurement Specialties, Inc., "Piezo Film Sensors Technical Manual," Apr. 1999.
International Search Report and Written Opinion; PCT/US/2008/087119; Feb. 18, 2009.
Supplementary European Search Report for EP Application No. 07869848.7, dated Oct. 18, 2010. 8 pgs.
Wikipedia, Quantum Tunnelling Composite. Retrieved on Mar. 10, 2016 from https://en.wikipedia.org/wiki/Quantum_tunnelling_composite. 3 pgs.

* cited by examiner

ABLATION ELECTRODE WITH TACTILE SENSOR

CROSS-REFERENCE TO RELATED APPLICATIONS

This application is related to U.S. application Ser. No. 11/647,314 filed 29 Dec. 2006; entitled "Pressure-Sensitive Conductive Composite Contact Sensor and Method for Contact Sensing"), now U.S. Pat. No. 9,579,483; Ser. No. 11/647,316 filed 29 Dec. 2006; entitled "Pressure-Sensitive Conductive Composite Electrode and Method for Ablation"), now U.S. Pat. No. 7,955,326; Ser. No. 11/647,294 filed 29 Dec. 2006; entitled "Pressure-Sensitive Conductive Composite Electrode and Method for Ablation"), now U.S. Pat. No. 7,883,508; and Ser. No. 11/553,965, filed 27 Oct. 2006 ("Systems and Methods for Electrode Contact Assessment), now U.S. Pat. No. 8,021,361, all of which are hereby incorporated by reference as though fully set forth herein.

BACKGROUND OF THE INVENTION a. Field of the Invention

The present invention pertains generally to an electrophysiological device and method for providing energy to biological tissue and, more particularly, to a contact sensor that is capable of being using with an ablation apparatus to provide greater contact sensitivity.

b. Background Art

Many medical procedures, including for example, creating lesions with electrical energy, rely on good contact between the medical device and the tissue. In some catheter applications, the point of electrode-tissue contact is as far as about 150 cm away from the point of application of force. This gives rise to functional and theoretical challenges associated with conventional devices, and thus, the ability to accurately assess tissue contact is increasingly important.

There is a need for contact sensing devices that provide greater contact sensitivity for control of medical treatments.

There is a need for improved sensor devices that provide greater contact sensitivity, especially in connection with RF ablation treatments.

BRIEF SUMMARY OF THE INVENTION

Disclosed herein is an electrode assembly having a catheter shaft, at least one tactile sensor; and an electrode at a distal end of the electrode assembly. The at least one tactile sensor is located between the catheter shaft and the electrode such that the tactile sensor will detect force that is applied to the electrode. The at least one tactile sensor may comprise two sensors, namely, a first tactile sensor that detects forces applied axially to the electrode assembly and a second tactile sensor that detects forces applied laterally to the electrode assembly. Further, each tactile sensor may be one that detects compression and stretching forces and generates an output signal that distinguishes a compression force applied to the tactile sensor from a stretching force applied to the tactile sensor. The assembly may include an analysis device coupled to the first and second tactile sensors such that it provides directional content information regarding the forces that are applied to the electrode. The output signal of each tactile sensor may be a signal with a magnitude that is proportional to the force applied to the tactile sensor. Optionally, the analysis device may provide information regarding the magnitude and direction of the forces that are applied to the electrode. The tactile sensor may be selected from the group consisting of: a pressure sensitive conductive composite sensor; a capacitance sensor; and a piezoelectric sensor. The tactile sensor may use a pressure sensitive conductive composite material.

Also disclosed is an electrode assembly having a catheter shaft, an ablation electrode at a distal end of the electrode assembly, and a plurality of tactile sensors located between the ablation electrode and the catheter shaft. Each of the plurality of tactile sensors may be in a plane that passes transverse to an axis of the electrode assembly. The plurality of sensors may detect longitudinal compression forces and transverse bending forces applied to the ablation electrode. Preferably, each of the plurality of tactile sensors generates a signal that is indicative of a characteristic selected from the group consisting of: resistance; capacitance; voltage; impedance; and combinations thereof. Preferably, the tactile sensors are selected from the group consisting of: a pressure sensitive conductive composite sensor; a capacitance sensor; a piezoelectric sensor; and combinations thereof. In a particular embodiment, each of the first and second tactile sensors may be a quantum tunneling conductive composite sensor. Of course, the tactile sensors may comprise a piezoelectric wire. In an optional embodiment, each of the plurality of tactile sensor generates an output signal in proportion to the compression force applied to the tactile sensor, and an output device may provide an indication of a direction of the force applied to the ablation electrode. For example, the output device may provide information on a direction and magnitude of the force applied to the ablation electrode.

Also disclosed is an ablation catheter for ablating tissue. The catheter has a catheter shaft, an ablation electrode at a distal end of the ablation catheter, and a plurality of tactile sensors located between the ablation electrode and the catheter shaft. The plurality of tactile sensors may be spaced evenly about a circumference of the ablation catheter, wherein each of the plurality of tactile sensor generates an output signal in proportion to the compression force applied to a portion of the ablation electrode. The catheter may include a controller configured to receive each of the output signals from the plurality of tactile sensors, wherein the controller analyzes the output signals and assesses a degree of contact between the ablation electrode and the tissue to be ablated. The ablation electrode is preferably electrically coupled to an ablation energy source such that the controller generates a control signal to activate the ablation energy source when the controller determines that the degree of contact between the ablation electrode and the tissue exceeds a preset contact threshold. Of course, the controller may also generate a control signal to deactivate the ablation energy source when the controller determines that the degree of contact between the ablation electrode and the tissue exceeds a preset maximum value. The sensor may be a pressure sensitive conductive composite sensor; a capacitance sensor; a piezoelectric sensor; and/or combinations thereof. For example, the tactile sensor may be made of quantum tunneling conductive composite material. In one embodiment, the ablation catheter may comprises at least four tactile sensors which are arranged in opposing pairs and are spaced evenly about a circumference of the electrode assembly.

Also disclosed is a method of sensing contact between a catheter and a tissue. For example, the method may include providing a catheter having a catheter shaft; an ablation electrode; and at least one tactile sensor located between the catheter shaft and the electrode. The catheter may be placed in contact with the tissue such that at least one force is exerted on the ablation electrode. The applied force may generate an output signal from each of the at least one tactile sensors; and further, may generate a signal that is indicative of a degree of contact between the catheter and the tissue. The control signal may be used to inhibit delivery of ablation energy if the degree of contact is below a preset contact threshold. Alternatively, the control signal may generate a control signal that activates delivery of ablation energy if the degree of contact is above a preset contact threshold. The method may also generate a control signal that deactivates delivery of ablation energy if the degree of contact is above a preset maximum value. When two sensors are used, the outputs can be compared such that an assessment may be made to determine whether the force is a lateral force. More particularly, the outputs may be compared in terms of impedance; resistance; capacitance; current and/or voltage. Multiple reference points may also be recorded. For example, the devices being used may be subjected to a first known amount of pressure such that the resulting output signal may be measured. This may be repeated for additional known forces. Then, if a unknown force is applied, the measurement information stored in data may be used to assess the degree of contact.

An object of the present invention is to provide a contact sensor assembly that can assess contact with tissue based on the degree of pressure that is exerted on the sensor.

Another object of the present invention is to provide a flexible contact sensor that measures pressure that is being exerted on the sensor based on direct or indirect contact between the sensor and another mass, such as tissue.

Yet another object of the present invention is to provide a method of contact sensing.

Yet another object of the present invention is to provide a method of manufacturing a contact sensor.

An objective of the present invention is to provide a pressure-sensitive, conductive composite-based sensor that may be used in connection with RF ablation treatment.

Another objective of the present invention is to provide a catheter having at least one tactile sensor that can assess whether sufficient contact exists between an ablation electrode and tissue to be ablated before ablation begins.

Yet another objective of the present invention is to provide a catheter having multiple tactile sensors that can asses a direction and magnitude of the forces being applied to the catheter.

Still another objective of the present invention is to provide a tactile force sensor that can measure the force asserted on an electrode by soft tissue.

Still another objective of the present invention is to provide a tactile force sensor that can assess contact based on resistance measurements using a PSCC sensor.

Still another objective of the present invention is to provide a tactile force sensor that can assess contact based on capacitance measurements using a capacitance sensor.

Still another objective of the present invention is to provide a tactile force sensor that can assess contact based on measurements using a piezoelectric sensor.

An objective of the present invention is to provide a QTC-based sensor that may be used in connection with RF ablation treatment.

Another object of the present invention is to provide a flexible, contact-sensitive sensor that can be used in a wide variety of tissue environments.

Yet another objective of this invention is to provide a method for practicing medical procedures using a pressure-sensitive, conductive polymer-based sensor in accordance with the teachings herein.

An advantage of using a PSCC in a contact sensor is that the design may be significantly less complicated, which permits reduced manufacturing costs and increased reliability.

The foregoing and other aspects, features, details, utilities, and advantages of the present invention will be apparent from reading the following description and claims, and from reviewing the accompanying drawings.

DETAILED DESCRIPTION OF THE INVENTION

Figure 1A:
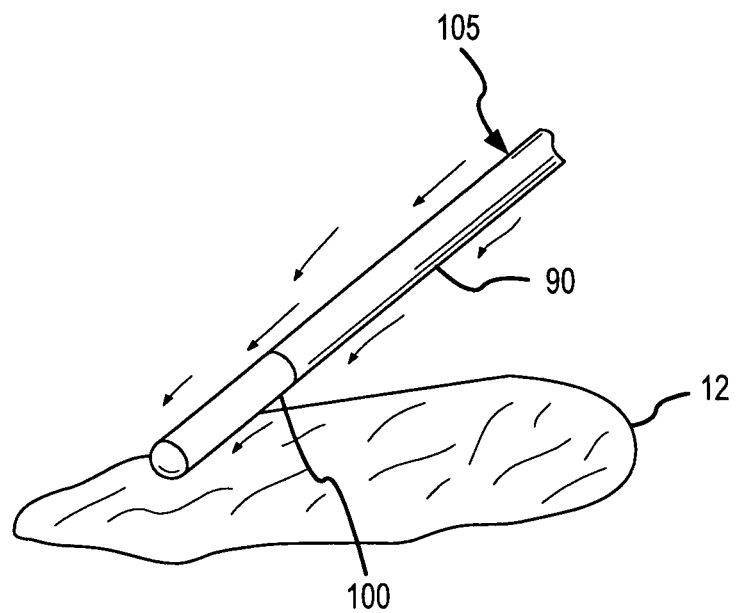
FIGS. 1A and 1B are perspective views of a representative embodiment of the present invention, illustrating how the present invention may be used to assess contact with tissue.

An ablation electrode having at least one tactile sensor is disclosed, together with a method of using and a method of manufacturing the ablation electrode. The present invention utilizes tactile sensors of three basic types: pressure sensitive conductive composite sensors; capacitance sensors; and piezoelectric sensors.

When used in this application, the terms "pressure sensitive conductive composite" and "PSCC" mean a pressure sensitive conductive composite that has unique electrical properties as follows: the electrical resistance of the PSCC varies inversely in proportion to the pressure that is applied to the PSCC. The PSCC material that is most useful with the present invention has a high electrical resistance when not under stress (that is, in a quiescent state), and yet the same PSCC material starts to become conductive under pressure, and indeed, the electrical resistance may fall to less than one ohm (1Ω) when under sufficient pressure. When in a quiescent state, the PSCC material preferably has a resistance that is greater than 100,000 ohms, and more preferably, greater than about 1 M ohms, and most preferably, the PSCC material is a non-conductor in its quiescent state (e.g., having a resistance greater than 10 M ohms). Preferably, the PSCC material will also meet cytotoxicity, hemolysis, systemic toxicity and intracutaneous injection standards.

The present invention will work with different PSCC materials. For example, U.S. Pat. No. 6,999,821 (which is incorporated by reference herein as if fully set forth below) discloses a conductor-filled polymer that may be useful in the present invention. As disclosed therein, conductor-filled polymers may include presently available materials approved for implantation in a human body such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637. The substrate need not be silicone; for example, it is contemplated that other insulating or weakly conductive materials (e.g., non-conductive elastomers) may be embedded with conductive materials, conductive alloys and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium and metals of the lanthanide and actinide series and if appropriate, at least one electroconductive agent). The conductive material may be in the form of powder, grains, fibers or other shaped forms. The oxides can be mixtures comprising sintered powders of an oxycompound. The alloy may be conventional or for example titanium boride.

Other examples of an acceptable PSCCs for use in the present invention include quantum tunneling composites ("QTC"), such as those available through Peratech Ltd. (of Darlington, UK), including the QTC pill, the QTC substrate and the QTC cables. The QTC materials designed by Peratech Ltd. have variable resistance values that range from greater than 10 M ohms (in the absence of stress) to less than 1 ohm when under pressure. Ideally, the QTC would meet cytotoxicity, hemolysis, systemic toxicity and intracutaneous injection standards.

Other examples of PSCC materials that may be used in the present invention include the conductive polymers described and disclosed in U.S. Pat. No. 6,646,540 ("Conductive Structures"); U.S. Pat. No. 6,495,069 ("Polymer Composition"); and U.S. Pat. No. 6,291,568 ("Polymer Composition"); all of the foregoing patents are incorporated by reference as if set forth below in their entireties. These materials are described as having a variable resistance of greater than $10^{12}$ Ohms before any stress is applied to less than 1 ohm when finger pressure is applied.

As a result of this unique property, PSCC materials may be described as having an ability to transform from an effective insulator to a metal-like conductor when deformed by compression, twisting, or stretching. The electrical response of a PSCC can be tuned appropriately to the spectrum of pressures being applied. Its resistance range often varies from greater than 10 MΩ to less than 1Ω. The transition from insulator to conductor often follows a smooth and repeatable curve, with the resistance dropping monotonically to the pressure applied. Moreover, the effect is reversible in the sense that once the pressure is removed, the electrical resistance is also restored. Thus, a PSCC may be transformed from an insulator to a conductor, and back to an insulator, simply by applying the appropriate pressure. PSCCs have been known to carry large currents (up to 10 Amps) and support large voltages (40 V and higher).

Preferably, the PSCC being used in connection with the present invention can transform from an insulator (that is, conducting little or no current) to an effective conductor simply by applying a small change in pressure to the PSCC. For example, by applying pressure with a hand, or more particularly, with a finger, a surgeon can transform the PSCC from an insulator to a conductor to permit contact sensing.

The PSCC used in the present invention may also be chosen or customized to be of a specific pressure sensitivity such that the transformation from an insulator to a conductor occurs over a wide or narrow range of pressure. For example, highly sensitive PSCCs, which register a sharp change in resistance with a small amount of applied pressure, may be preferred for soft contact applications such as the atrial wall. Less sensitive PSCCs, which require more pressure to register the same amount of change in resistance, may be preferred for hard contact applications such as ablation in ventricular walls.

The unique properties of a PSCC permit the creation of novel and pressure-sensitive current-control devices for evaluating tissue contact. The unique properties also permit the creation of novel and pressure-sensitive sensors to assess contact between the sensors and tissue that may be the subject of ablation.

Capacitance sensors utilize a probe that senses changes in capacitance to assess contact. Typically, driver electronics are used to convert the changes in capacitance into voltage changes, such that a device can indicate and/or record the resulting voltage change. In its most basic form, a capacitor consists of two conductive plates separated by a dielectric medium. The capacitor stores energy in the form of an electric field, and the ability to store energy is measured in capacitance. A capacitance sensor monitors capacitance which will vary in response to a stimuli such as touch. A force on a capacitance sensor typically reduces the senor's ability to store energy, resulting in a measurable change. With a capacitance sensor, the sensor surface is the electrified plate and when pressure is applied, the resulting change in capacitance can be measured and quantified.

Piezoelectric sensors utilize a piezoelectric material, which generates an electrical voltage when the material is placed under stress. A piezoelectric sensor can be used to measure the voltage that results when a piezoelectric material is placed under strain. Piezoelectric materials can be made in a variety of forms, including for example, piezoelectric wire, piezoelectric film, and piezoelectric tubes.

Figure 1B:
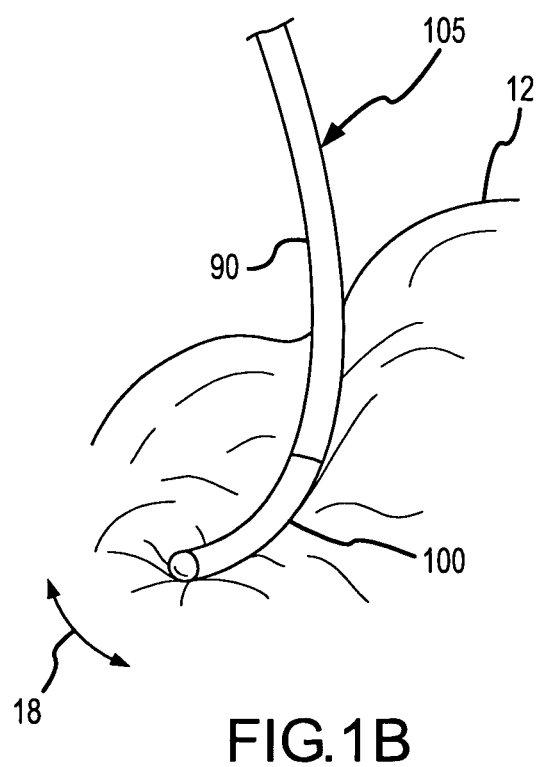

FIGS. 1A and 1B illustrate a sample embodiment of the present invention. As illustrated in FIGS. 1A and 1B, PSCC contact sensor 105 includes a catheter shaft 90 and a contact surface 100 that extends from catheter shaft 90. In this embodiment, contact sensor 105 is flexible such that when it comes into contact with tissue 12, contact sensor 105 is deflected in direction 18 as illustrated in FIG. 1*b*, and the deflection permits the degree of contact between contact sensor 105 and tissue 12 to be assessed.

Figure 2:
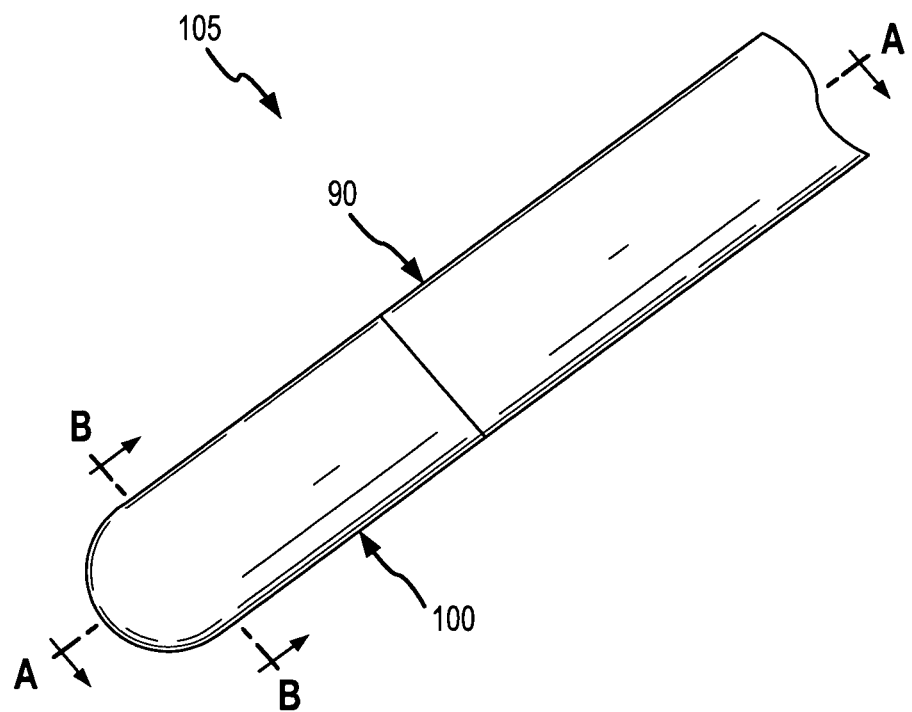
FIG. 2 is a side view drawing of an exemplary catheter having a PSCC sensor.

FIG. 2 is a close-up of the sample embodiment depicted in FIGS. 1A and 1B. FIG. 2 illustrates cross-sectional reference lines A-A and B-B, which will be used to illustrate preferred embodiment of the present invention.

Figures 3A, 3B:
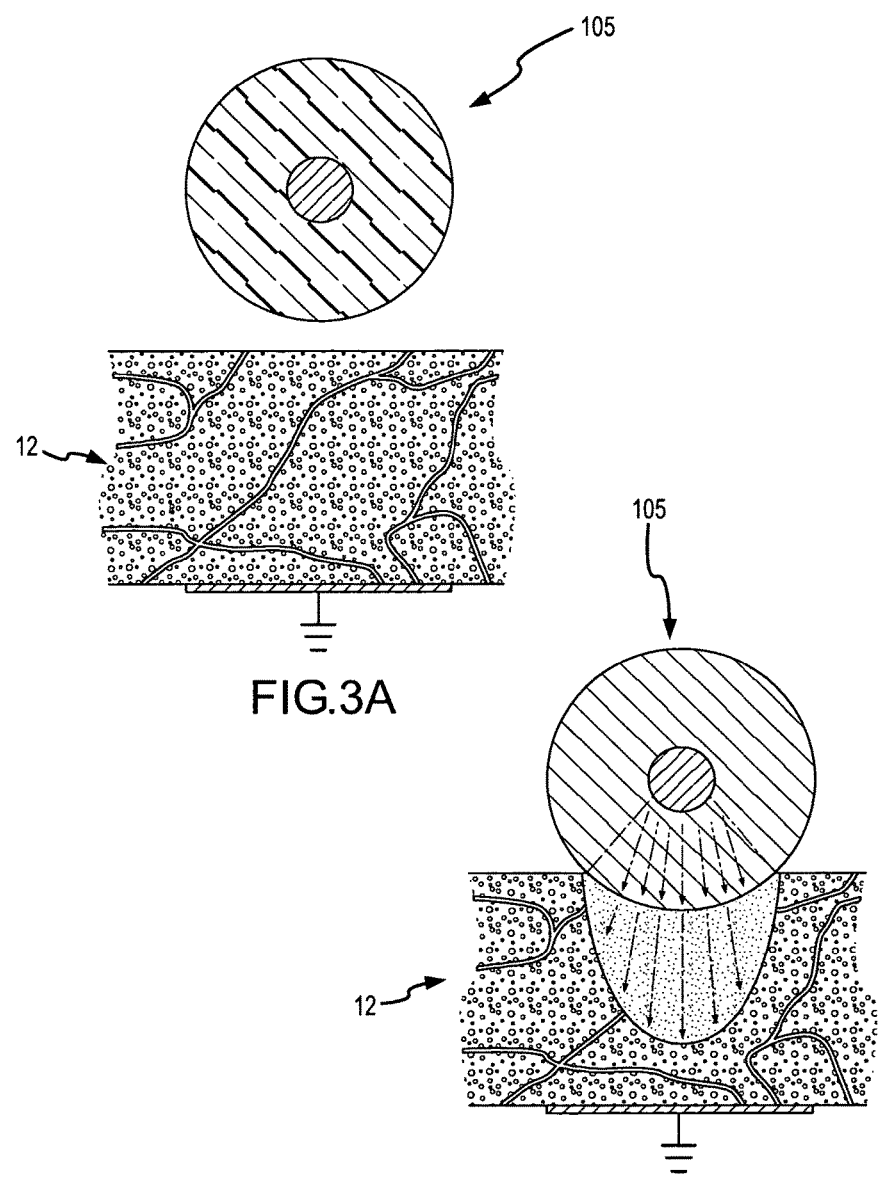
FIGS. 3A and 3B are cross sectional views that demonstrate the contact pressure at the sensor-tissue interface.

As illustrated in FIG. 3A, when the PSCC sensor is in a relatively contact free environment (such as air, or in the flowing blood stream while inside a blood vessel or heart chamber), the PSCC is an insulator. When used for a sensing application, however, the PSCC sensor is placed against tissue as illustrated in FIG. 3B. As the contact pressure increases, the PSCC becomes conductive and permits the degree of contact to be assessed by the sensing device. Because of the unique properties of a PSCC, only that portion of the PSCC sensor that is in contact with the tissue becomes conductive. Those portions which are not in direct contact with the tissue, such as the region facing the blood, remain non-conductive, thereby mitigating any current leakage that may cause coagulum and thrombus formation.

The resistance of a PSCC sensor changes anisotropically, based on the variation of the contact pressure on the PSCC sensor. Thus, as illustrated in FIG. 3B, the contact pressure at the sensor-tissue interface is maximum at the point (or line) of normal incidence and gradually decreases along the arc of contact to zero at the edge of the contact. Because of its ability to detect stress forces in any direction, the sensor can be designed to be omni-directional in use.

Figure 4A:
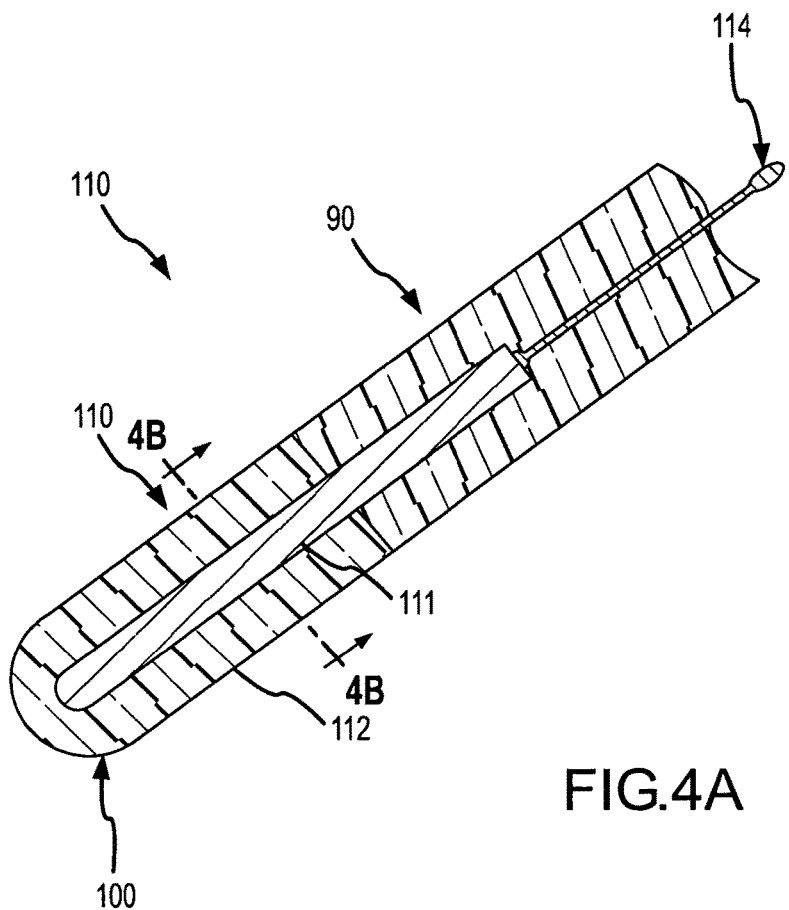
FIGS. 4A and 4B are cross-sectional views of a preferred embodiment of a catheter having a PSCC sensor.
Figure 4B:
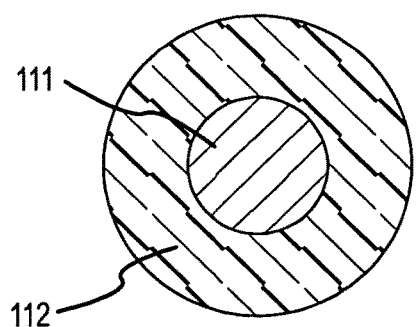

FIGS. 4A and 4B illustrate a preferred embodiment of the present invention, revealing two cross sectional drawings taken along the reference lines of A-A and B-B as labeled in FIG. 2.

In FIGS. 4A and 4B, PSCC contact sensor 110 includes a catheter shaft 90 and a contact surface 100 that extends from catheter shaft 90. Catheter shaft 90 may be either conductive or non-conductive, and preferably, catheter shaft 90 is non-conductive. In this embodiment, the PSCC forms the working surface of the sensor that is used for contact assessment. As depicted in FIGS. 4A and 4B, PSCC sensor 110 comprises: flexible inner conductive core 111; and an outer PSCC substrate layer 112, which is mechanically and electrically coupled to the flexible inner conductive core 111. Flexible inner conductive core 111 may include a flat top (like the top of a right cylinder), or optionally it may include a portion of a sphere on its distal end as illustrated in FIG. 4A. Flexible inner conductive core 111 may be connected to an electrical conductor 114, which may be connected to an analyzer (not shown). In use, this preferred embodiment is used to assess contact between PSCC sensor 110 and tissue (not shown) to which a reference electrode (not shown) has been attached. PSCC sensor 110 assesses the contact between contact surface 100 and the subject tissue by monitoring the electrical characteristics between two nodes, namely, the reference electrode (not shown) and the flexible inner conductive core 111 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 110. Preferably, the reference electrode is grounded to an electrical ground reference signal.

Figure 5A:
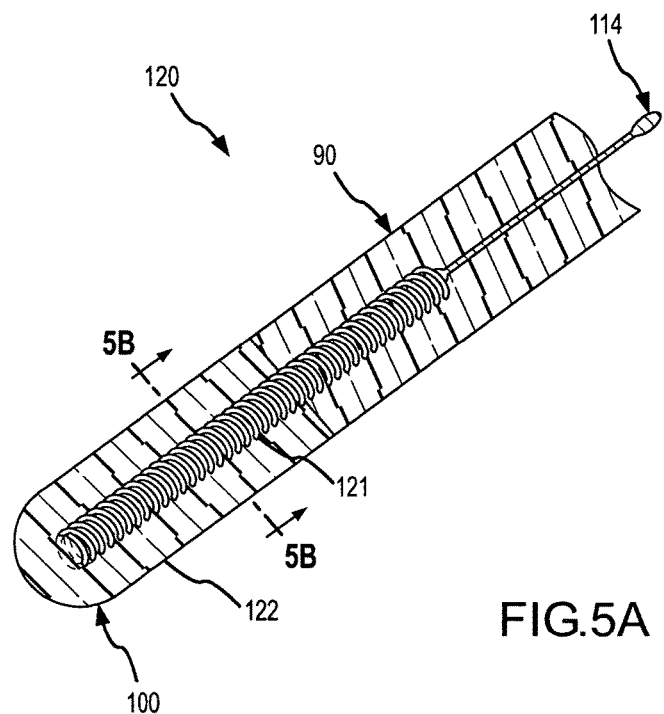
FIGS. 5A and 5B are cross-sectional views of a preferred embodiment in which the PSCC sensor is in the shape of a helix.
Figure 5B:
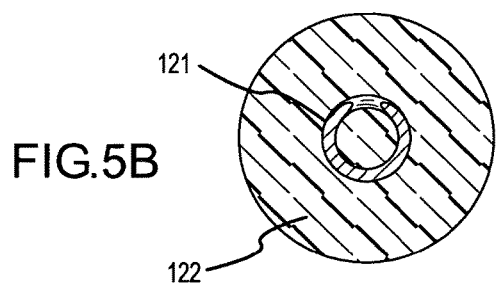

FIGS. 5A and 5B illustrate another preferred embodiment of the present invention, revealing two cross sectional drawings taken along the reference lines of A-A and B-B as labeled in FIG. 2. PSCC sensor 120 extends from a catheter shaft 90, and PSCC sensor 120 comprises: flexible inner conductive coil 121 in the shape of a helix; and a PSCC substrate layer 122 within which the inner conductive coil 121 is located. Flexible inner conductive coil 121 is connected to an electrical conductor 114, which may be connected to an analyzer (not shown). In use, this preferred embodiment is used to assess contact between PSCC sensor 120 and tissue (not shown) to which a reference electrode (not shown) has been attached. PSCC sensor 120 assesses the contact between contact surface 100 and the subject tissue by monitoring the electrical characteristics between two nodes, namely, the reference electrode (not shown) and the flexible inner conductive coil 121 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 120. Preferably, the reference electrode is grounded to an electrical ground reference signal.

Figure 6A:
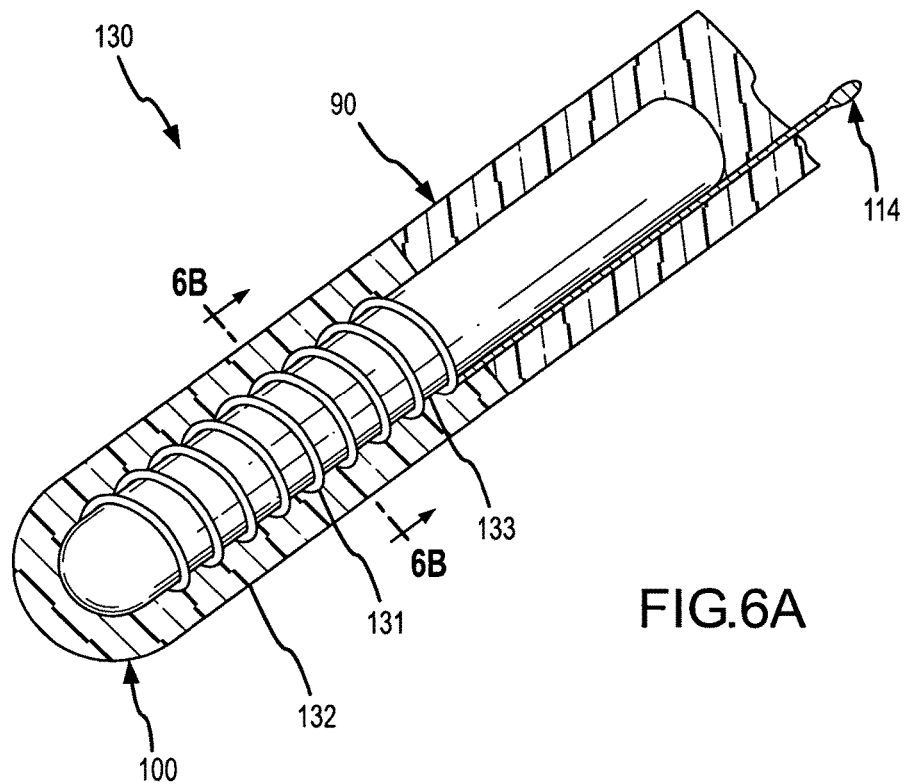
FIGS. 6A and 6B are cross-sectional views of another preferred embodiment in which the PSCC sensor is located about an inner conductive core.
Figure 6B:
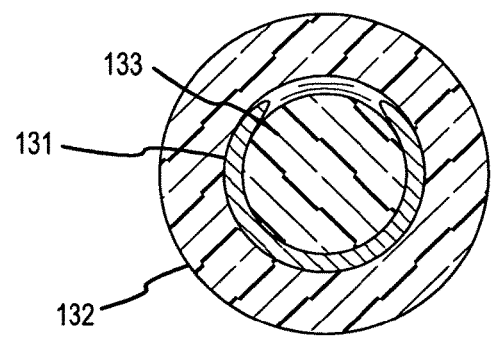

FIGS. 6A and 6B illustrate yet another preferred embodiment of the present invention, revealing two cross sectional drawings taken along the reference lines of A-A and B-B as labeled in FIG. 2. PSCC sensor 130 extends from a catheter shaft 90, and PSCC sensor 130 comprises: flexible inner conductive coil 131 in the shape of a helix; an outer PSCC substrate layer 132; and an electrically insulative flexible shaft 133 located within the helix of the flexible inner conductive coil 131. Flexible shaft 133 may optionally include a portion of a sphere on its distal end as shown in FIG. 6A. Flexible inner conductive coil 131 is connected to an electrical conductor 114, which may be connected to an analyzer (not shown). In use, this preferred embodiment is used to assess contact between PSCC sensor 130 and tissue (not shown) to which a reference electrode (not shown) has been attached. PSCC sensor 130 assesses the contact between contact surface 100 and the subject tissue by monitoring the electrical characteristics between two nodes, namely, the reference electrode (not shown) and the flexible inner conductive coil 131 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 130. Preferably, the reference electrode is grounded to an electrical ground reference signal.

Figure 7A:
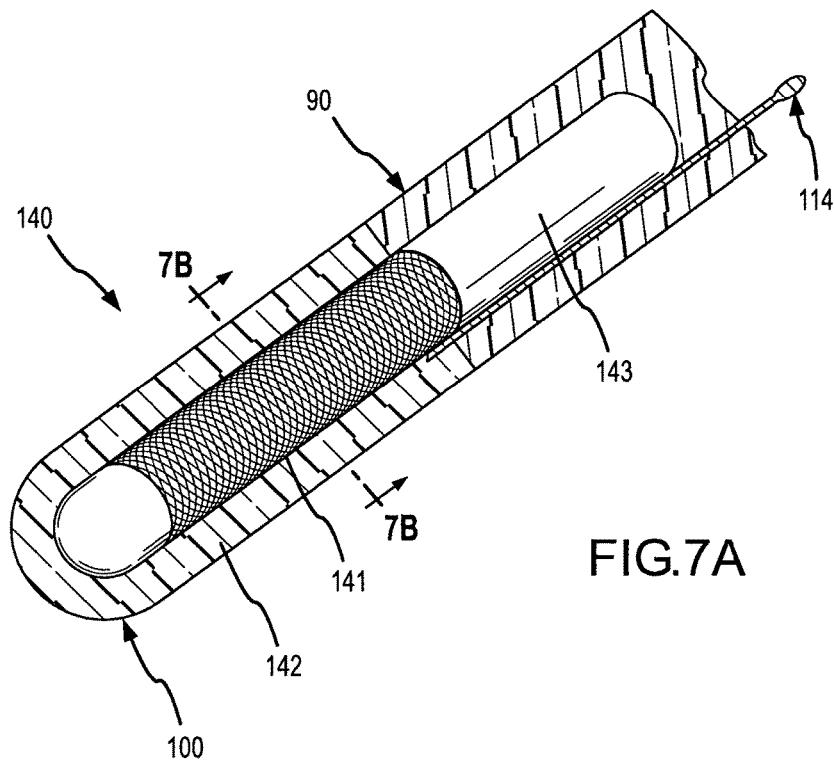
FIGS. 7A and 7B are cross-sectional views of another preferred embodiment in which the PSCC sensor is in the shape of a mesh.
Figure 7B:
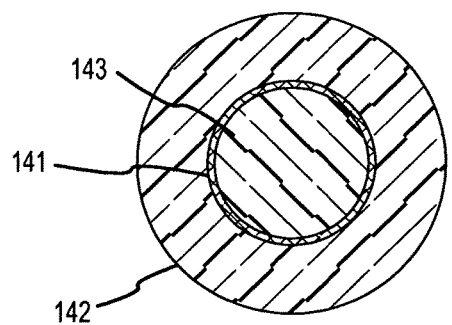

FIGS. 7A and 7B illustrate yet another preferred embodiment of the present invention, revealing two cross sectional drawings taken along the reference lines of A-A and B-B as labeled in FIG. 2. PSCC sensor 140 extends from a catheter shaft 90, and PSCC sensor 140 comprises: flexible inner conductive sheath 141 formed of a mesh; an outer PSCC substrate layer 142; and an electrically insulative flexible shaft 143 located interiorly of the flexible inner conductive sheath 141. Flexible shaft 143 may optionally include a portion of a sphere at its distal end as shown in FIG. 7A. Flexible sheath 141 is connected to an electrical conductor 114, which may be connected to an analyzer (not shown). In use, this preferred embodiment is used to assess contact between PSCC sensor 140 and tissue (not shown) to which a reference electrode (not shown) has been attached. PSCC sensor 140 assesses the contact between contact surface 100 and the subject tissue by monitoring the electrical characteristics between two nodes, namely, the reference electrode (not shown) and the flexible sheath 141 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 140. Preferably, the reference electrode is grounded to an electrical ground reference signal.

Figure 8A:
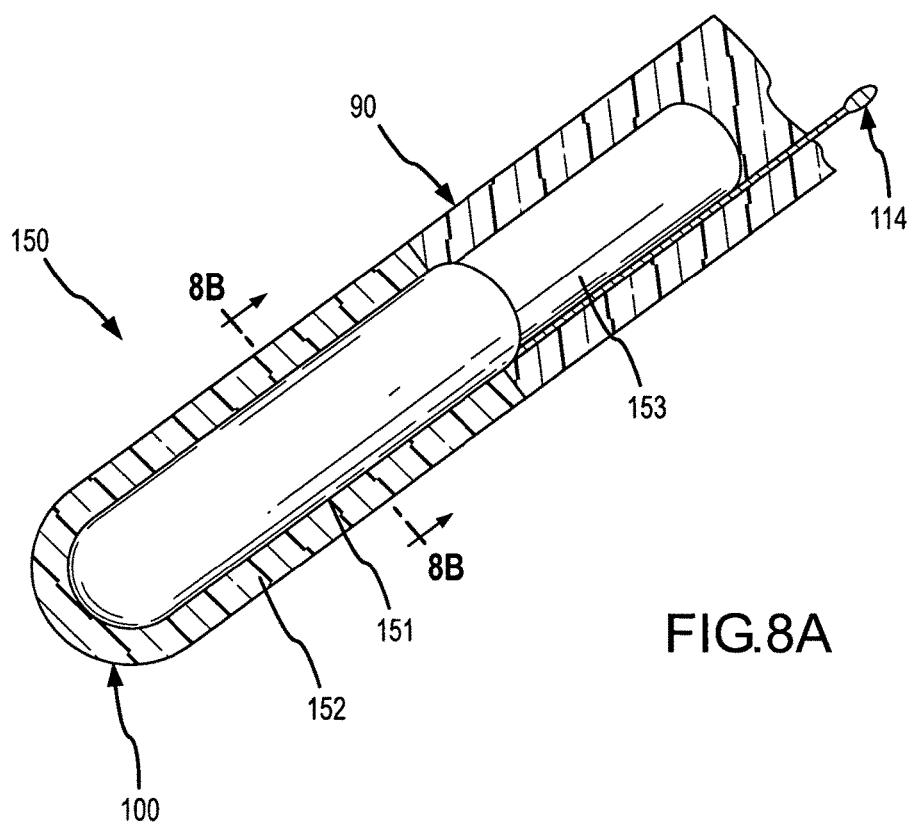
FIGS. 8A and 8B are cross-sectional views of another preferred embodiment in which the PSCC sensor is formed as an outer substrate layer.
Figure 8B:
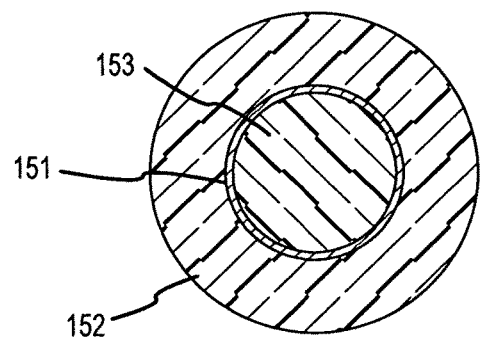

FIGS. 8A and 8B illustrate yet another preferred embodiment of the present invention, revealing two cross sectional drawings taken along the reference lines of A-A and B-B as labeled in FIG. 2. PSCC sensor 150 extends from a catheter shaft 90, and PSCC sensor 150 comprises: an electrically insulative flexible shaft 153; a flexible inner conductive layer 151 (formed, for example, as a coating and/or wrap around flexible shaft 153); and an outer PSCC substrate layer 152. Electrically insulative flexible shaft 153 and flexible inner conductive layer 151 may optionally include a portion of a sphere at their respective distal ends (as illustrated in FIG. 8A). Flexible inner conductive core 151 is connected to an electrical conductor 114, which may be connected to an analyzer (not shown). In use, this preferred embodiment is used to assess contact between PSCC sensor 150 and tissue (not shown) to which a reference electrode (not shown) has been attached. PSCC sensor 150 assesses the contact between contact surface 100 and the subject tissue by monitoring the electrical characteristics between two nodes, namely, the reference electrode (not shown) and the flexible inner conductive core 151 (which is preferably measured using electrical conductor 114). By way of example, an analyzer (such as an impedance, resistance, capacitance or other electrical measurement device) may be used to measure the electrical characteristics present on electrical conductor 114 relative to the reference electrode (not shown) secured to the tissue being contacted with PSCC sensor 150. Preferably, the reference electrode is grounded to an electrical ground reference signal.

Figure 9A:
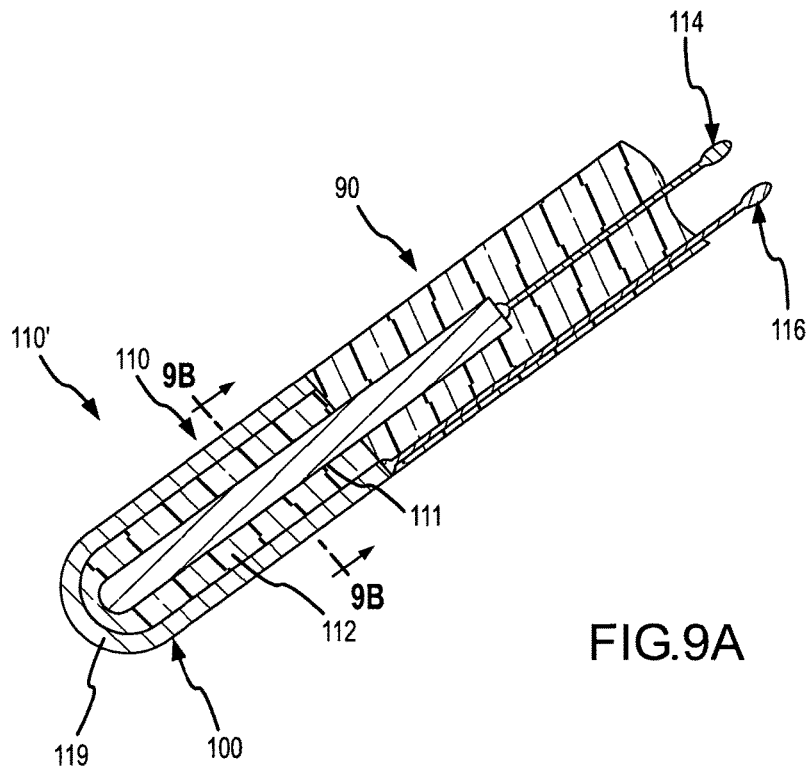
FIGS. 9A and 9B are cross-sectional views of a preferred embodiment of a catheter having a PSCC sensor.
Figure 9B:
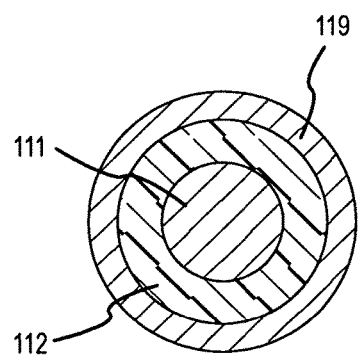

FIGS. 9A and 9B illustrate a preferred embodiment of the present invention, revealing two cross sectional drawings taken along the reference lines of A-A and B-B as labeled in FIG. 2. FIG. 9A is a variation of the preferred embodiment illustrated in FIG. 4A. In FIGS. 9A and 9B, PSCC contact sensor 110' includes a catheter shaft 90 and a contact surface 100 that extends from catheter shaft 90. Catheter shaft 90 may be either conductive or non-conductive, and preferably, catheter shaft 90 is non-conductive. As depicted in FIG. 9A, PSCC sensor 110' comprises: flexible inner conductive core 111; and an outer PSCC substrate layer 112, which is mechanically and electrically coupled to the flexible inner conductive core 111. Flexible inner conductive core 111 may optionally include a portion of a sphere on its distal end, as illustrated in FIG. 9A. Flexible inner conductive core 111 may be connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 110' and tissue by monitoring the electrical characteristics between two nodes, namely, the conductive outer layer 119 (which is preferably measured using electrical conductor 116) and the flexible inner conductive core 111 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 10A:
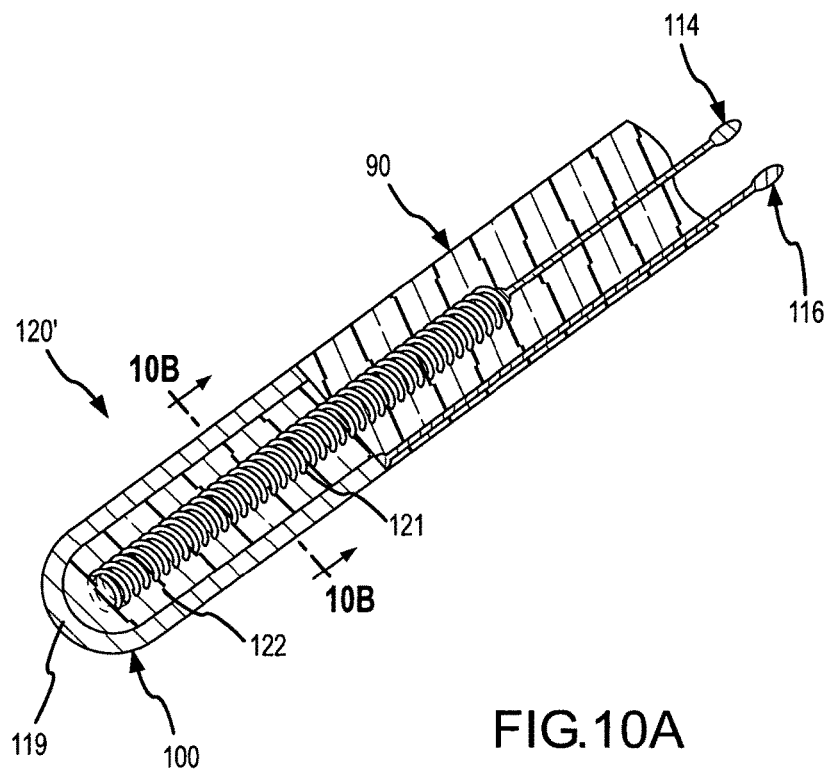
FIGS. 10A and 10B are cross-sectional views of another preferred embodiment in which the PSCC sensor is in the shape of a helix.
Figure 10B:
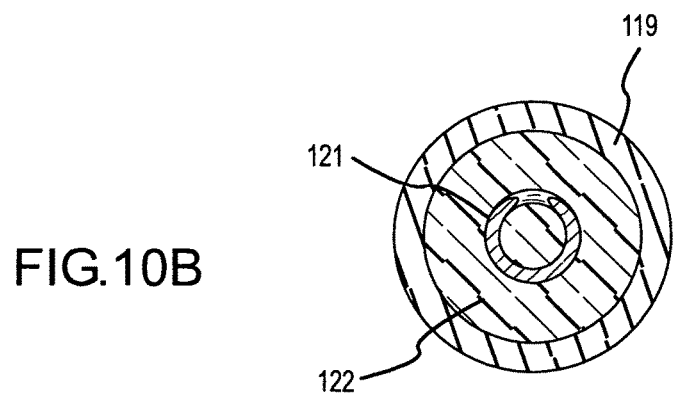

FIGS. 10A and 10B illustrate another preferred embodiment of the present invention, revealing two cross sectional drawings taken along the reference lines of A-A and B-B as labeled in FIG. 2. FIG. 10A is a variation of the preferred embodiment illustrated in FIG. 5A. PSCC sensor 120' extends from a catheter shaft 90, and PSCC sensor 120' comprises: flexible inner conductive coil 121 in the shape of a helix; and a PSCC substrate layer 122 within which the inner conductive coil 121 is located. Flexible inner conductive coil 121 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 120' and tissue by monitoring the electrical characteristics between two nodes, namely, the conductive outer layer 119 (which is preferably measured using electrical conductor 116) and the flexible inner conductive coil 121 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 11A:
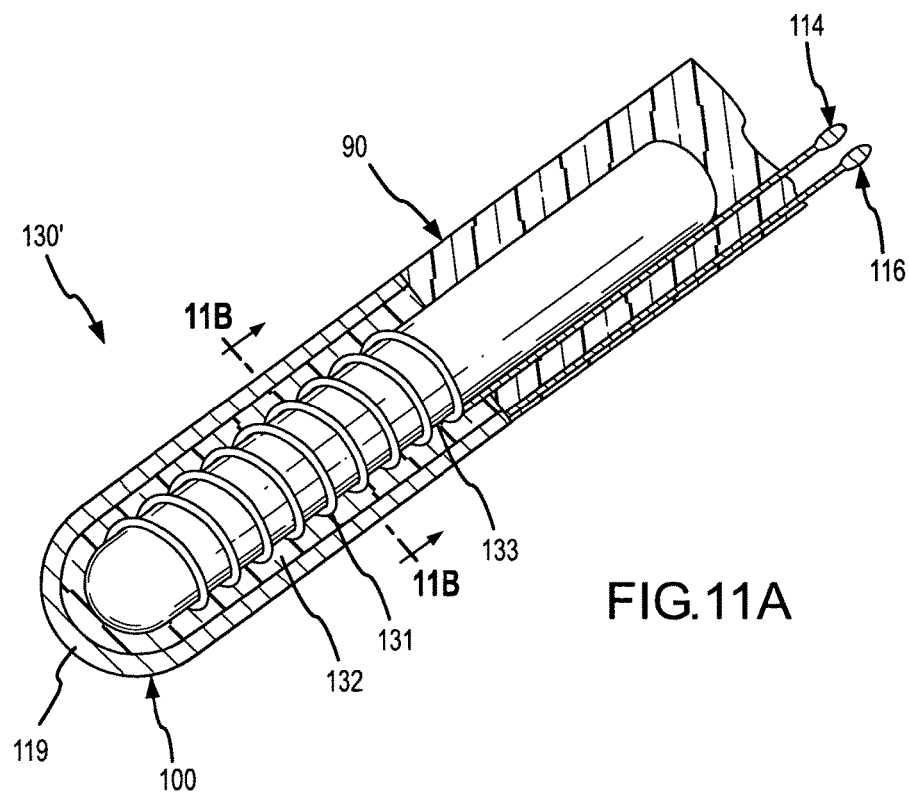
FIGS. 11A and 11B are cross-sectional views of another preferred embodiment in which the PSCC sensor is located about an inner conductive core.
Figure 11B:
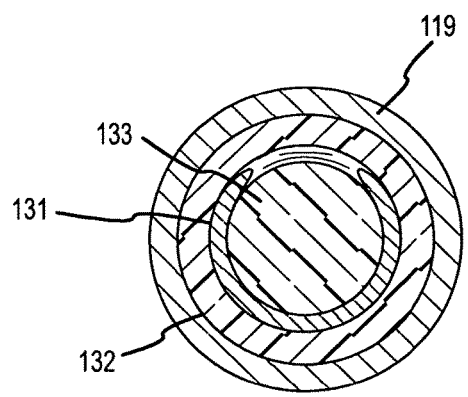

FIGS. 11A and 11B illustrate yet another preferred embodiment of the present invention, revealing two cross sectional drawings taken along the reference lines of A-A and B-B as labeled in FIG. 2. FIG. 1A is a variation of the preferred embodiment illustrated in FIG. 6A. PSCC sensor 130' extends from a catheter shaft 90, and PSCC sensor 130' comprises: flexible inner conductive coil 131 in the shape of a helix; an outer PSCC substrate layer 132; and an electrically insulative flexible shaft 133 located within the helix of the flexible inner conductive coil 131. Flexible shaft 133 may optionally include a portion of a sphere on its distal end as shown in FIG. 11A Flexible inner conductive coil 131 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 130' and tissue by monitoring the electrical characteristics between two nodes, namely, the conductive outer layer 119 (which is preferably measured using electrical conductor 116) and the flexible inner conductive coil 131 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 12A:
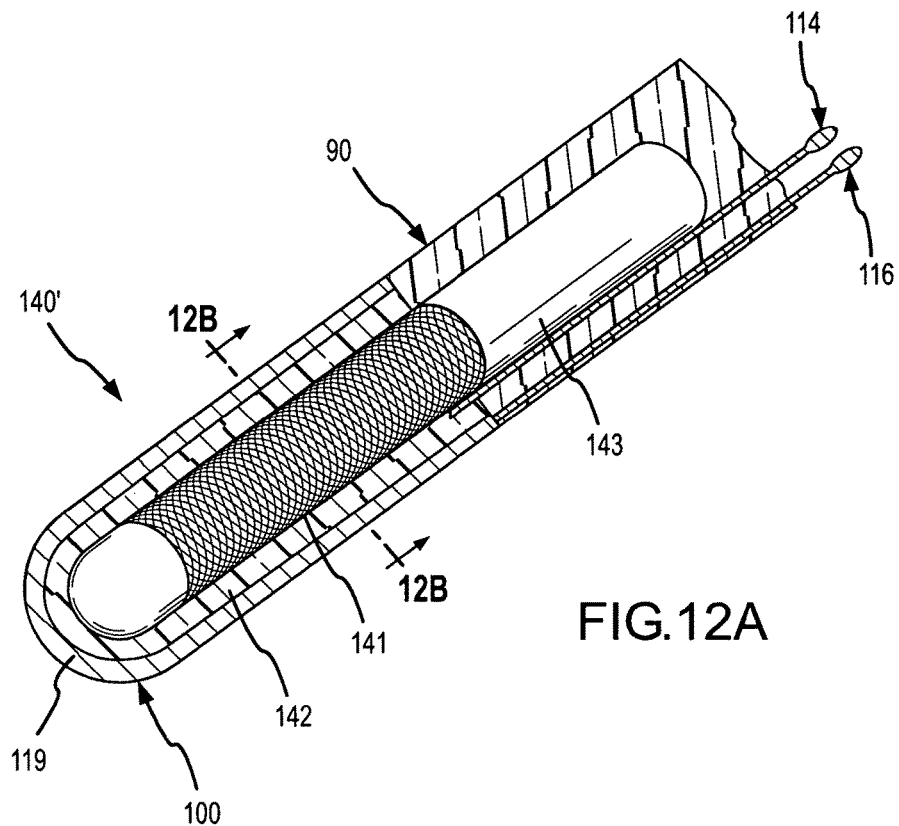
FIGS. 12A and 12B are cross-sectional views of another preferred embodiment in which the PSCC sensor is in the shape of a mesh.
Figure 12B:
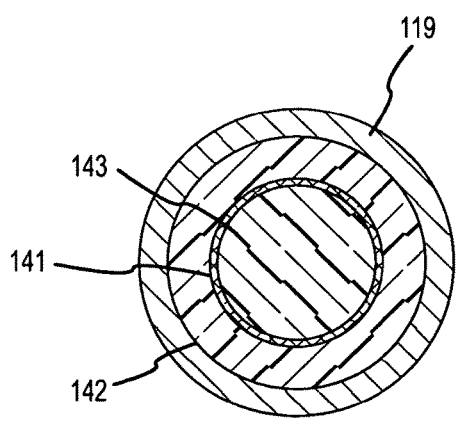

FIGS. 12A and 12B illustrate yet another preferred embodiment of the present invention, revealing two cross sectional drawings taken along the reference lines of A-A and B-B as labeled in FIG. 2. FIG. 12A is a variation of the preferred embodiment illustrated in FIG. 7A. PSCC sensor 140' extends from a catheter shaft 90, and PSCC sensor 140' comprises: flexible inner conductive sheath 141 formed of a mesh; an outer PSCC substrate layer 142; and an electrically insulative flexible shaft 143 located interiorly of the flexible inner conductive sheath 141. Flexible shaft 143 may optionally include a portion of a sphere at its distal end as shown in FIG. 7A. Flexible sheath 141 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 140' and tissue by monitoring the electrical characteristics between two nodes, namely, the conductive outer layer 119 (which is preferably measured using electrical conductor 116) and the flexible sheath 141 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Figure 13A:
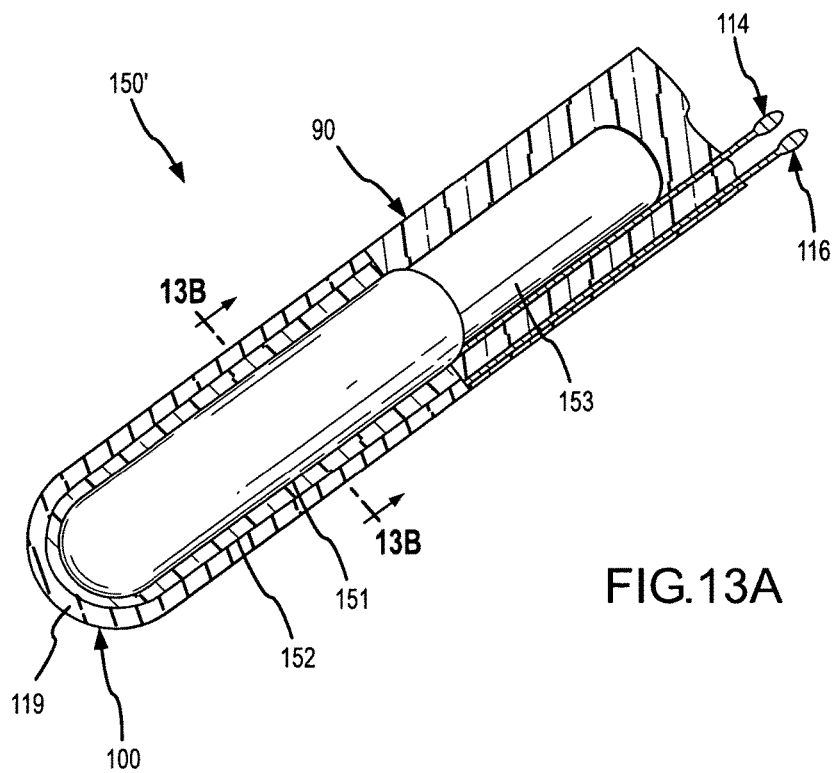
FIGS. 13A and 13B are cross-sectional views of another preferred embodiment in which the PSCC sensor is formed as an outer substrate layer.
Figure 13B:
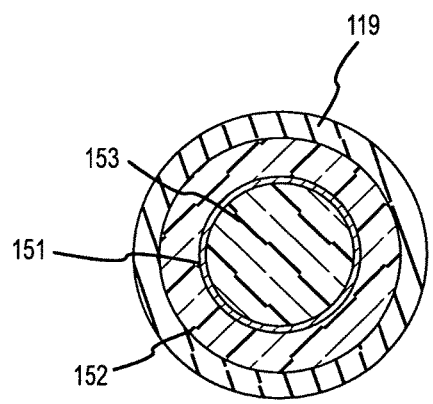

FIGS. 13A and 13B illustrate yet another preferred embodiment of the present invention, revealing two cross sectional drawings taken along the reference lines of A-A and B-B as labeled in FIG. 2. FIG. 13A is a variation of the preferred embodiment illustrated in FIG. 8A. PSCC sensor 150' extends from a catheter shaft 90, and PSCC sensor 150' comprises: an electrically insulative flexible shaft 153; a flexible inner conductive layer 151 (formed, for example, as a coating and/or wrap around flexible shaft 153); and an outer PSCC substrate layer 152. Electrically insulative flexible shaft 153 and flexible inner conductive layer 151 may optionally include a portion of a sphere at their respective distal ends (as illustrated in FIG. 13A). Flexible inner conductive core 151 is connected to an electrical conductor 114, which may be connected to an analyzer (not shown). PSCC substrate layer 112 is covered by a conductive outer layer 119, which may be connected to an electrical conductor 116; conductive outer layer 119 may be flexible, rigid, or it may offer an intermediate degree of flexibility. In use, this preferred embodiment is used to assess contact between PSCC sensor 150' and tissue by monitoring the electrical characteristics between two nodes, namely, the conductive outer layer 119 (which is preferably measured using electrical conductor 116) and the flexible inner conductive core 151 (which is preferably measured using electrical conductor 114). By way of example, an analyzer (such as an impedance, resistance, capacitance or other electrical measurement device) may be used to measure the electrical characteristics present on electrical conductor 114 relative to electrical conductor 116.

Electrical conductors 114 and 116 may be implemented using a single conductive wire or multiple strands of wire. Preferably, the wires may be made of flexible conductive materials which allow the surface contacting area to be bent and formed into various shapes to provide better contact to the tissue. Acceptable materials include, but are not limited to, stainless steel, nickel titanium (nitinol), tantalum, copper, platinum, iridium, gold, or silver, and combinations thereof. Preferably, the material used to manufacture the conductive element is a bio-compatible electrically conductive material, such as platinum, gold, silver, nickel titanium, and combinations thereof. Other electrically conductive materials coated with bio-compatible materials may also be employed, including for example, gold-plated copper. Finally, it is also contemplated that electrically conductive polymers may also be used provided they are bio-compatible or coated with a bio-compatible material.

Figure 14:
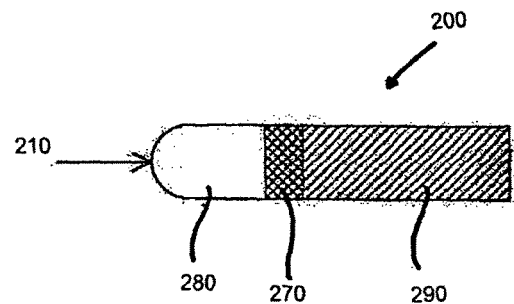
FIG. 14 is a cross-sectional view of a preferred embodiment having a single tactile sensor.

A further embodiment of the present invention is disclosed in connection with FIG. 14, namely, an ablation electrode assembly 200, which includes catheter shaft 290, ablation electrode 280 and tactile sensor 270 positioned there between. Catheter shaft is typically formed with a non-electrically conductive outer layer and may have one or more lumens internally of the shaft. Ablation electrode 280 may be formed of a wide variety of materials including, but not limited to, stainless steel, nickel titanium (nitinol), tantalum, copper, platinum, iridium, gold, or silver, and combinations thereof. Preferably, the material used to manufacture the ablation electrode is a bio-compatible electrically conductive material, such as platinum, gold, silver, nickel titanium, and combinations thereof. Other electrically conductive materials coated with bio-compatible materials may also be employed, including for example, gold-plated copper. Finally, it is also contemplated that electrically conductive polymers may also be used provided they are bio-compatible or coated with a bio-compatible material.

In a typical operation, ablation assembly 200 may be used to ablate cardiac tissue, and thus, ablation electrode 280 may be pressed into contact with the myocardium. When the ablation electrode 280 is in sufficient contact with the myocardium, the myocardium exerts a force 210 to the ablation electrode 280, mostly along the longitudinal axis. The force is delivered by ablation electrode 280 to tactile sensor 270, which is preferably soft and sufficiently sensitive to measure the small force applied to ablation electrode 280.

Tactile sensor 270 may be one of three types of sensors: a pressure sensitive conductive composite sensor; a capacitance sensor; and a piezoelectric sensor. A PSCC sensor may utilize any number of the PSCC materials and embodiments described above. Preferably the sensor includes, or may be coupled to, a device for measuring the resistance of the tactile sensor 270. Of course, a capacitance sensor and/or a piezoelectric sensor may be used, in which case the sensor preferably includes, or may be coupled to, a device for measuring the capacitance and/or voltage of the tactile sensor 270. As described above, the three types of sensors work on different physical principles. For example, a PSCC material responds to pressure such that its resistance (or impedance) changes, and may transform from a non-conductor to a conductor. A capacitance sensor changes it capacitance based on pressure, and similarly a piezoelectric sensor varies its output voltage based on the degree of pressure applied to the surface of the sensor.

In many applications, the ablation catheter 200 will be placed in contact with a tissue surface such that the ablation catheter is orthogonal to the tissue surface, resulting in an axial force 210 being applied to the ablation electrode 280. When the force is axial, a single tactile sensor 270 will often be sufficient to assess the contact between ablation electrode 280 and the tissue to be ablated.

For example, if tactile sensor 270 is a PSCC sensor, then the force 210 will cause the resistance of tactile sensor 270 to drop, and the extent to which it decreases may be used to assess the degree of contact between ablation electrode 280 and the tissue being treated. Similarly, if tactile sensor 270 is a capacitance sensor, then the force 210 will cause the capacitance of tactile sensor 270 to drop, and the extent to which it decreases may be used to assess the degree of contact between ablation electrode 280 and the tissue being treated. If tactile sensor 270 is a piezoelectric sensor, then the force 210 will cause the voltage generated by tactile sensor 270 to change (depending on the configuration, it may increase or decrease), and the extent of the change may be used to assess the degree of contact between ablation electrode 280 and the tissue being treated.

In other applications, it is possible that the force applied to the catheter is a transverse force, in which case a single tactile sensor 270 as illustrated in ablation electrode 200 may be inadequate to assess the contact.

Figure 15:
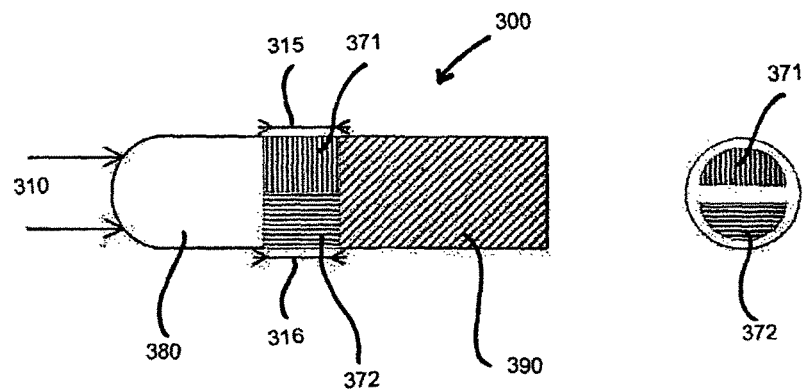
FIGS. 15 and 16 are cross-sectional views of a preferred embodiment having two tactile sensors.
Figure 16:
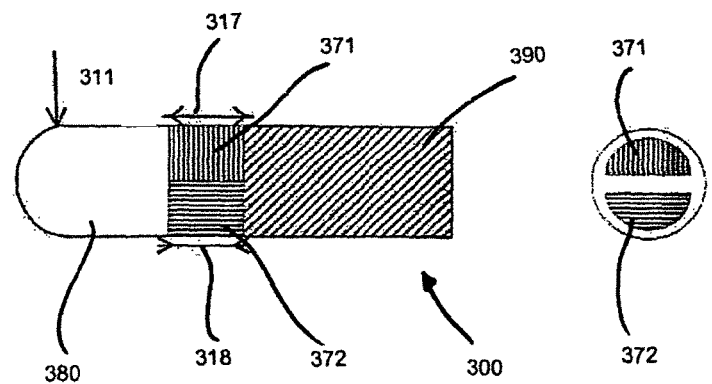

FIGS. 15-16 depict an ablation assembly 300 with two tactile sensors 371, 372 interposed between ablation electrode 380 and catheter shaft 390. First tactile sensor 371 and second tactile sensor 372 are positioned side by side, which is very useful in practice. When axial force 310 is applied to ablation electrode 380 as illustrated in FIG. 15, both tactile sensors 371, 372 are compressed by compressing forces 315, 316, and if axial force 310 is perfectly axial, then tactile sensors will experience approximately equal compressing forces.

When transverse force 311 is applied as illustrated in FIG. 16, tactile sensors 371, 372 are affected differently. As illustrated, first tactile sensor 371 will experience a pulling or stretching (that is, tensile) force 317, whereas second tactile sensor 372 will experience a compression force 318. Depending on the type of tactile sensor being used, the compression and stretching forces could result in changes that move in opposite directions, and a measurement device (such as a computer or other processor) can deduce useful information about these changes. For example, as illustrated in FIG. 16, detecting a tensile force 317 on first tactile sensor 371, while simultaneously detecting a compression force 318 on second tactile sensor 372, will permit the measurement device to determine that a lateral force 311 is being applied (based on opposite forces being detected) and further that the direction is downward (or more particularly, in a direction of travel from first tactile sensor 371 to second tactile sensor 372. Thus, the use of two tactile sensors permits the device to distinguish between an upward lateral force, a downward lateral force, as well as an axial force (relatively equal forces being applied to both tactile sensors).

Applying the teachings herein, one of ordinary skill would appreciate that additional tactile sensors could be employed in the ablation electrode, in which case, the electrode could glean additional directional content out of the applied forces. By way of example, and without limiting the number of tactile sensors to be used with the present invention, a catheter may be implemented using four tactile sensors, each arranged to be located within a quadrant of the electrode (or in other words, being spaced about a circumference and about 90 degrees apart). Such an arrangement would permit the assessment of forces in at least three directions.

Of course, the tactile sensors used by the present inventions will also permit one to determine the magnitude of forces being applied to the ablation electrode. Generally, the change effected in the electrical characteristics of the tactile sensor will vary proportionately with the force being applied. When used in this context, the term "proportional" in intended to be construed broadly to encompass all proportionality relationships and constants.

It is also contemplated that the present invention may monitor the impedance of a tactile sensor, for example, in the event that a measurement device applied an alternating voltage to a PSCC sensor. The teachings above would be easily applied to impedance measurements.

In operation, any of the devices above could be used to effect an ablation treatment. For example, the ablation device depicted in FIG. 14 would be placed in contact with a tissue surface to permit the degree of contact to be assessed by measuring one of the resistance, capacitance, voltage, and/or impedance. Based on the measured electrical characteristic, the device could readily generate a signal that is indicative of a degree of contact that exists between the catheter and the tissue. Further, if the measured characteristics were deemed to be associated with a pressure that is below a minimum pressure threshold, a control signal could be generated to preclude ablation (e.g., inhibit the generator's output of ablation energy). Similarly, if the pressure were deemed to be above a particular threshold (for example, because the resistance of a PSCC material had dropped too low), then a signal could be generated that would inhibit ablation.

In some circumstances it may be permissible to preclude ablation based on the orientation of the ablation electrode to the tissue. For example, if it is determined that a bending force is being applied to the ablation electrode, then the electrode may not have a desired angle of contact with the surface to be ablated. At such an angle, ablation may not create the proper lesion. Thus, ablation could be inhibited until a proper angle of contact is detected.

The present invention permits the construction of a flexible, pressure sensitive contact assessment device that can be used in a wide variety of different tissue environments, including for example, tissues having varying degrees of elasticity and contour.

The present invention permits the construction of a flexible sensor to measure pressure that is applied to the sensor, for example, pressure that may be applied to the sensor by the myocardium. Such sensors may be used to measure the pressure that is applied directly to the sensor, or depending on the configuration of the sensor, it may measure the pressure that is applied to a component that is in contact with the sensor (as may be the case when an additional element is disposed between a PSCC-based sensor and tissue that is exerting pressure on the additional element). In the case where a PSCC-based sensor is positioned within a catheter, the PSCC-based sensor is preferably used to measure pressure that is applied axially to catheter. Of course, the PSCC based sensor could be oriented in order to measure pressure that is applied transversely to the catheter.

While the preferred embodiments disclosed in the attached figures disclose a contact sensor that is generally cylindrical in shape, the present invention also contemplates that the contact sensor may be formed into various shapes to better fit the contour of the target tissue. In one embodiment, for example, the contact sensor can be made long enough to strap around and form a noose around the pulmonary veins in epicardial applications. Particularly, the conductive element that is coupled to the PSCC (for example, reference numbers 111, 121, 131, 141, and 151) may be formed into a desired shape and then the PSCC layer will be formed over the conductive element in the preferred shape. For example, the contact sensor may be shaped like a spatula for certain applications, including for example, minimally invasive sub-xyphoid epicardial applications, where the spatula shape will permit easy placement and navigation in the pericardial sac. Because PSCC can be made to be a flexible material, it can be used to form electrodes having a great variety of shapes, including a spatula.

Alternatively, the conductive element that is coupled to the PSCC may be formed using shape-memory retaining material, such as nitinol, which would permit the electrode to be fitted to specific preset geometries, such as the ostium of a pulmonary vein, such that the electrode is shaped to provide a desired contact pressure pattern on the tissue due to the deformation of the wire when pressed against the tissue.

Similarly, while the reference to insulative shaft (for example, 133, 143, and 153) is generally used in connection with a generally cylindrical member, it is contemplated by the present invention that the insulative shaft could be in a geometric shape other than a cylinder, including, for example, a noose, a spatula, or the shape of the ostium of a pulmonary vein. For purposes of this application, the term "insulative shaft" is intended to encompass shapes in addition to a cylindrical shaft.

Whenever it is desired that the conductive element that is coupled to the PSCC may be formed in the shape of a helix, such as is the case with elements 121, and 131, the coil may be chosen to be of a specific stiffness (i.e., having a characteristic spring constant) that would allow the coil to exert a desired amount of pressure on the PSCC when the electrode bends or deflects upon contact with the tissue. One of skill in the art would understand that the degree of desired contact pressure would depend in part upon the elastic property of the tissue being contacted with the electrode. For example, the atrial wall may require less contact pressure than the ventricular wall. Thus, electrodes of varying stiffness can be designed for application in different tissues and different regions of the heart.

In some embodiments, for example, as depicted in FIGS. 5, 6 and 7, the conductive element may be mounted on an insulative shaft. The conductive element can be shaped in any number of ways, including for example, a coil, mesh, coating or wrap. The insulative shaft provides additional mechanical support in applications that require greater amounts of axial pressure and torque. The insulative shaft may be made of any electrically insulative material, including, for example, polyurethane. Preferably, the insulative shaft is made of a biocompatible, electrically insulative material.

The embodiments described above can be used with a processor such that the processor may provide more precise information about the pressures being encountered by the embodiment. In particular, any of the sensors described above may be used with a memory device to record information regarding one or more forces that are applied to the sensor. For example, a first known pressure may be applied to the contact sensor and a first measurement of an electrical characteristic may be made such that the first known pressure may be associated with the first measurement. Similarly, a second known pressure may be applied to the contact sensor and a second measurement of an electrical characteristic may be made such that the second known pressure may be associated with the second measurement. Additional known pressures may be applied and additional corresponding measurements may be made and associated. Then, if an unknown pressure is applied, the processor may use the known pressures and their respective associated measurements to help quantify the unknown pressure, for example by interpolating or extrapolating the value of the unknown pressure from the known pressures.

While the embodiments above are discussed in the context of applied pressure, the embodiments above can also be used to assess forces relative to contact between tissue and the contact sensor. Pressure is simply a measurement of the force per unit area, and thus, to assess force, the surface area of a contact surface must be known or be capable of being determined or calculated. The force information may be derived from the information available on forces and the contact surface area.

Though not depicted, it is contemplated that each of the embodiments discussed above may optionally be used in connection with one or more electrically-conductive, outer protective coverings. Preferably, the outer covering is electrically conductive, such as a flexible wire mesh, a conductive fabric, a conductive polymer layer (which can be porous or nonporous), or a metal coating. The outer covering may be used to not only increase the mechanical integrity, but to enhance the contact sensor's ability to assess the tissue contact (for example, when measuring electrical characteristics using a reference electrode connected to the target tissue). In some cases, the outer covering may be made using a biocompatible material in order to help make the overall assembly biocompatible.

Though not depicted, it is also contemplated that in certain sensor configurations, it may be desirable to optionally use an electrically non-conductive outer protective covering. In such cases, an outer covering that is electrically insulative, such as a non-conductive polymer layer (which can be porous or nonporous), may be used to increase the mechanical integrity. In some cases, the outer covering may be made using a biocompatible material in order to help make the overall assembly biocompatible. Such an electrically-non-conductive covering may also serve as a pressure transfer element to more evenly distribute pressure to the pressure sensitive conductive composite member.

One of ordinary skill will appreciate that while the PSCC materials may be designed to respond to a variety of stresses, the principles and embodiments herein may be adapted to respond to specific stress forces, for example, axial forces, orthogonal forces, twisting forces, compressing forces, stretching forces, etc., without deviating from the scope of the present invention.

While many of the embodiments above are discussed in the context of a PSCC sensor, the same principles can be applied to devices having tactile sensors of a non-PSCC material.

Although multiple embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:
1. A catheter, comprising:
  a catheter shaft comprising a distal portion and a proximal portion, wherein the catheter shaft comprises at least one tactile sensor that extends longitudinally along at least a portion of the catheter shaft, and
  at least one electrode,
  wherein the at least one tactile sensor comprises an inner non-conductive shaft surrounded by a flexible conductive coil, wherein the flexible conductive coil is operably connected to an electrical conductor,
  and wherein the flexible conductive coil is surrounded by a layer comprising a pressure sensitive conductive composite material.

2. The catheter of claim 1, wherein the electrical conductor comprises a plurality of conductive wires.

3. The catheter of claim 1, wherein the at least one tactile sensor comprises a pressure sensitive conductive composite sensor, a capacitance sensor, or a piezoelectric sensor.

4. The catheter of claim 1, wherein the at least one electrode comprises a second tactile sensor.

5. The catheter of claim 4, wherein the second tactile sensor is a capacitance sensor.

6. The catheter of claim 1, wherein the at least one tactile sensor is contained entirely within a portion of the catheter shaft and proximal of the distal portion, and wherein the electrode is an ablation electrode.

7. The catheter of claim 6, wherein the at least one tactile sensor is located between the distal portion of the catheter shaft and the ablation electrode.

\* \* \* \* \*